(12) United States Patent
Binder

(10) Patent No.: US 7,767,458 B2
(45) Date of Patent: Aug. 3, 2010

(54) METHOD FOR DETERMINING COAGULATION ACTIVATION AND DEVICE FOR CARRYING OUT SAID METHOD

(75) Inventor: Bernd Binder, Vienna (AT)

(73) Assignee: Technoclone Gesellschaft m.b.H., Vienna (AT)

( * ) Notice: Subject to any disclaimer, the term of this patent is extended or adjusted under 35 U.S.C. 154(b) by 0 days.

(21) Appl. No.: 11/884,966

(22) PCT Filed: Feb. 22, 2006

(86) PCT No.: PCT/AT2006/000073

§ 371 (c)(1),
(2), (4) Date: Mar. 10, 2008

(87) PCT Pub. No.: WO2006/089324

PCT Pub. Date: Aug. 31, 2006

(65) Prior Publication Data

US 2008/0194036 A1 Aug. 14, 2008

(30) Foreign Application Priority Data

Feb. 22, 2005 (AT) ............................ A 296/2005
Oct. 11, 2005 (AT) ............................ A 1656/2005

(51) Int. Cl.
*G01N 33/86* (2006.01)
*G01N 33/48* (2006.01)

(52) U.S. Cl. .................... 436/69; 436/63; 436/164; 436/172; 422/73; 422/82.08; 435/13; 600/369; 73/64.41; 73/64.43

(58) Field of Classification Search ............... 436/43, 436/45, 47, 63, 71, 164, 165, 166, 172, 69; 422/63, 64, 68.1, 73, 82.05, 82.08; 435/2, 435/13; 600/369; 73/64.41, 64.43
See application file for complete search history.

(56) References Cited

U.S. PATENT DOCUMENTS

| | | | | |
|---|---|---|---|---|
| 5,314,695 A * | 5/1994 | Brown | ........................ | 424/450 |
| 5,418,143 A * | 5/1995 | Zweig | ........................ | 435/13 |
| 5,625,036 A * | 4/1997 | Hawkins et al. | ............. | 530/381 |
| 6,124,110 A | 9/2000 | Wöber et al. | | |
| 6,183,979 B1 * | 2/2001 | Lee et al. | ....................... | 435/13 |
| 6,203,816 B1 * | 3/2001 | Brown | ........................ | 424/450 |
| 6,248,353 B1 * | 6/2001 | Singh | ........................ | 424/450 |
| 6,596,543 B2 * | 7/2003 | Wang et al. | .................. | 436/69 |
| 6,733,985 B1 * | 5/2004 | Lee | ............................. | 435/13 |
| 7,049,087 B2 * | 5/2006 | Jenny et al. | ................... | 435/13 |
| 2003/0232075 A1 * | 12/2003 | Nelsestuen | ................. | 424/450 |

FOREIGN PATENT DOCUMENTS

JP 06148182 A 5/1994
WO WO 99/66939 12/1999

* cited by examiner

*Primary Examiner*—Maureen M Wallenhorst
(74) *Attorney, Agent, or Firm*—Andrew Wilford

(57) ABSTRACT

A method is disclosed of assaying circulating microparticles contained in a sample of whole blood or blood plasma from a patient to determine the patient's ability to generate thrombin or Factor Xa as blood-clotting factors, wherein the circulating microparticles are microparticles of platelets, endothelial cells, monocytes, and smooth muscle cells, which carry on their surfaces both negatively charged phospholipids as well as tissue factor. The results of the assay may be used to determine the ability of the patient to generate thrombin or Factor Xa as blood clotting factor based upon the circulating microparticles.

8 Claims, 14 Drawing Sheets

| Test | Peak thrombin nM | Slope (nM/min) |
|---|---|---|
| Normal Control Plasma | 353.2 ± 19.6 | 56.0 ± 8.54 |
| Thrombophilia | 437.7 ± 9.38 | 92.2 ± 0.04 |

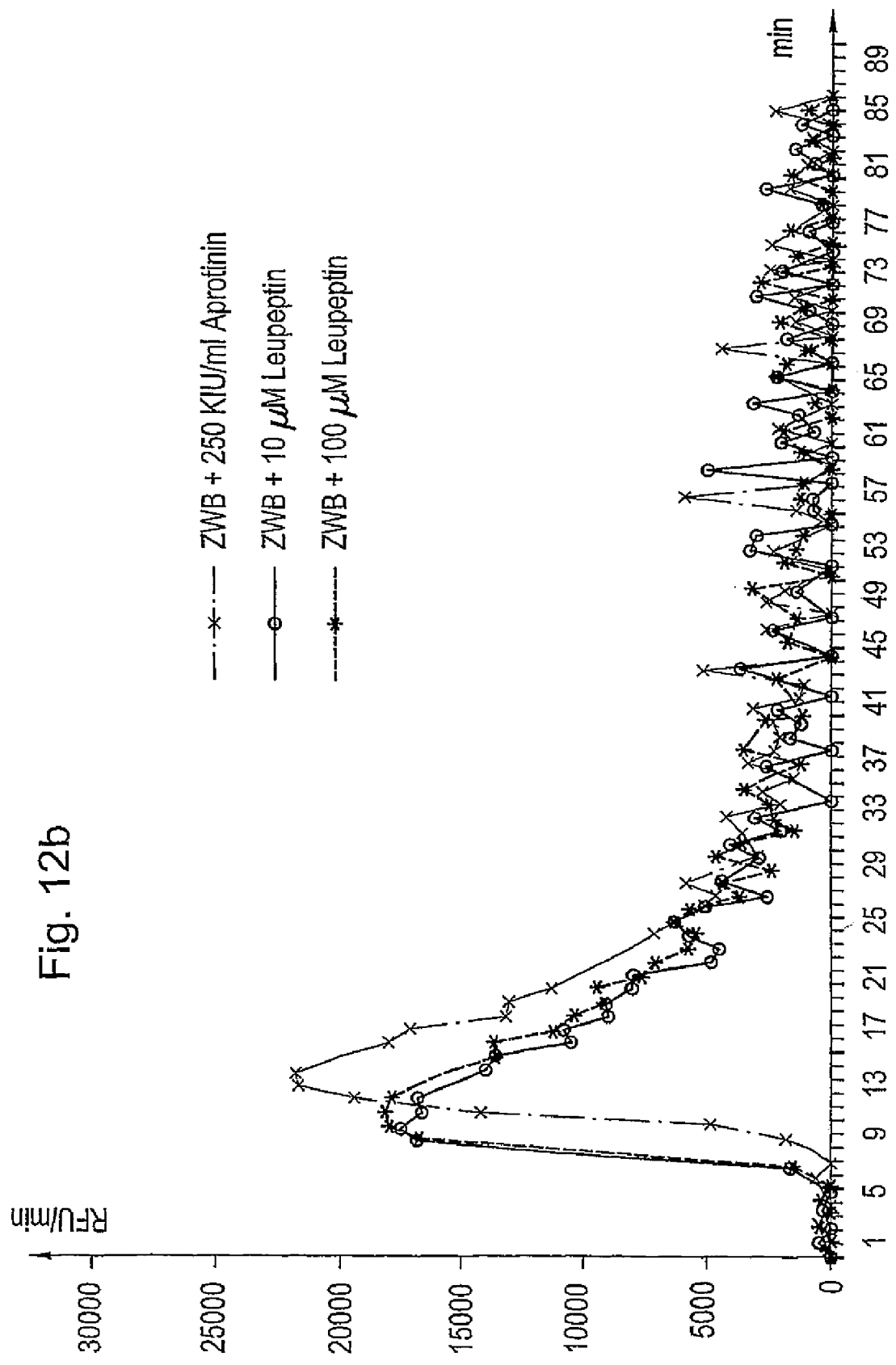

US 7,767,458 B2

METHOD FOR DETERMINING COAGULATION ACTIVATION AND DEVICE FOR CARRYING OUT SAID METHOD

CROSS REFERENCE TO RELATED APPLICATIONS

This application is the US national Phase of PCT/AT 2006/000073 filed 22 Feb. 2006 claiming the benefit of the priority of Austrian Patent Application AT 296/2005 filed 22 Feb. 2005 and Austrian Patent Application AT 1656/2005 filed 11 Oct. 2005.

FIELD OF THE INVENTION

The present invention concerns a procedure for the determination of the activation of the coagulation system. The invention concerns also equipment for the execution of the procedure for parallel determination of thrombin generation by means of fluorescence measurement and for classical conventional coagulation parameters with a rotating cuvette plate.

BACKGROUND OF THE INVENTION

Current State of Knowledge

The principle of thrombin generation is for a long time well-known and is also often used for the determination of coagulation activity ([1-8]). It is unknown that by use of different concentrations of added tissue factor (0 to >100 pM) but in each case identical phospholipid micelles to samples with different number of platelets and/or circulating micro particles it is possible to draw conclusions on the functional activity of plasmatic factors of the clotting system and the amount and activity of microparticles contained in the sample. Thereby this assay allows also to determine circulating microparticles. Circulating micro particles were found before several years and are made responsible for the activation of the coagulation system under certain situations. These situations are kidney diseases accompanied coagulation disorders ([9]), diseases during pregnancy (Eclampsie ([10-12])), the metabolic syndrome ([13]), diabetes and thrombotic syndromes during atherosclerosis ([14-16]). The determination of circulating micro particles was so far primarily made via quantitative isolation of the micro particle by means of differential centrifugation from the plasma, via FACS analysis of circulating micro particle using marker proteins or by means of an ELISA system in which the negatively charged phospholipids (phosphatidylserine, PS) that are exposed on micro particles are used to bind to Annexin V immobilized on micro titer plates ([17-22]). All these procedures are however time-consuming and permit no direct simple quantification of the micro particles. The procedure described here permits quantification of the circulating micro particles due to their functional characteristic of thrombin generation.

SUMMARY OF THE INVENTION

The procedure according to this invention is characterized by the fact that coagulation is initiated by addition of phospholipids micelles, with no or different quantities of tissue factor and as measure for the activation of the coagulation system the formation of activated factor X or of thrombin is used. Formation of activated factor X or of thrombin is determined by a suitable synthetic substrate. By determination of the formation of activated coagulating factors (factor Xa or thrombin) in whole blood or plasmas with different platelet counts (platelet-rich plasma, platelet-poor plasma and platelet-free plasma) and activation of the coagulating system with or without addition of tissue factor it is possible to detect not only coagulating defects (different forms of hemophilia), or anti-coagulation therapy (patient under anticoagulation therapy, heparin therapy or therapy with direct thrombin or factor Xa inhibitors) but also to evaluate patients with thrombophilia (antithrombin III deficiency, protein C deficiency, protein S deficiency, mutation of factor $v_{Leiden}$) and to conclude on the number and activity of circulating cellular micro particles in the samples. The possibility to detect by means of this test system also circulating micro particles, is based on the characteristic of micro particles to stimulate dose-dependently thrombin generation, since these micro particles posses clotting-activating properties (Phosphatidylserine, tissue factor and others).

The invention concerns further equipment for the execution of the procedure for the parallel determination of thrombin generation by means of fluorescence measurement and for classical conventional coagulation parameters with a rotating cuvette plate, which equipment is characterized by the fact that into the cuvette plate a cuvette ring is inserted, whereby at least in one part of the cuvette ring a measuring station for at least two fluorescence measuring positions and at least four conventional measuring positions for coagulating, chromogenic substrates and turbidimetric measurements are placed.

BRIEF DESCRIPTION OF THE DRAWINGS

FIGS. 12a, 12b and 12c are series of graphs showing over time thrombin generation in a sample of whole blood with the benefit of adding different protease inhibitors, or mixtures thereof, in different concentrations, where the results are interpretable only in the presence of the protease inhibitors.

TEST PRINCIPLE

Figure 1:
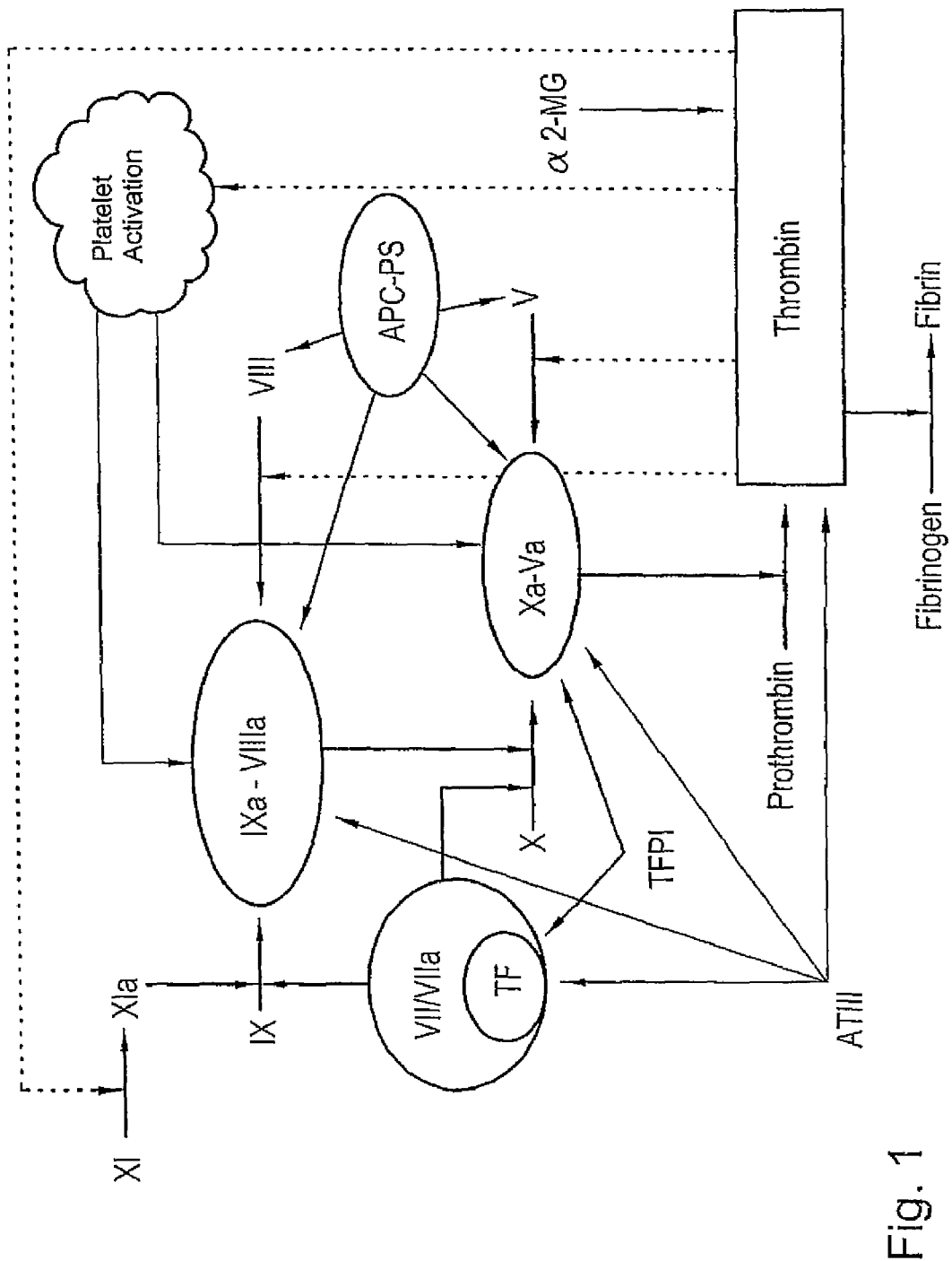
FIG. 1 is a schematic diagram showing the coagulation cascade, including all precursors, leading up to the production of thrombin and fibrin.

The principle of the test is based on the fact that the initiation of thrombin generation in the plasma by phospholipid micelles loaded which tissue factor takes place after addition of calcium chloride; if phospholipid micelles without tissue factor are added, the initiation of clotting takes place by micro particle contained in the sample, which contain tissue factor. The formed thrombin leads in a positive feedback to the activation of, among others, factor V and VIII, whereby thrombin generation is substantially accelerated. The formed thrombin, or the likewise formed factor Xa can be quantified by means of a suitable synthetic substrate is. The amount of formed thrombin or factor Xa correlates with the amount of added phospholipid micelles and/or of tissue factor contained in the sample and is dependent on the function of plasmatic coagulation factors and their inhibitors (FIG. 1. depicts a coagulation scheme with factors, which are determined by thrombin generation).

EXAMPLES

Example 1

Determination of the Degree of Anti-Coagulation by Means of the Thrombin Generation Assay (TGA)

Figure 2:
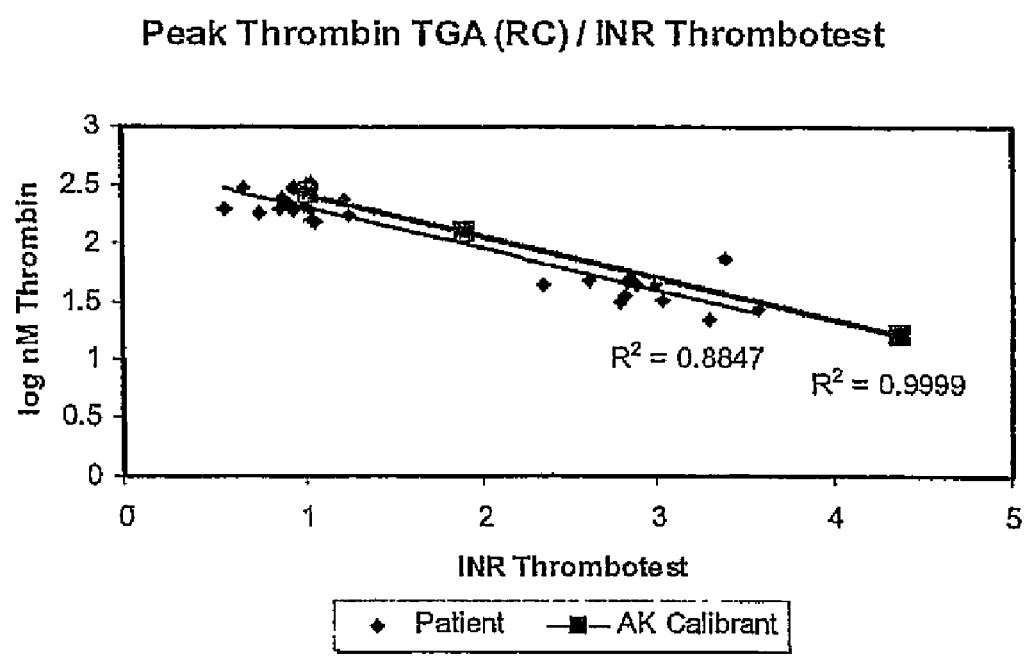
FIG. 2 shows the correlation between coagulation time ratios (INR) measured by a classical thromboplastin reagent (Thrombotest) and peak thrombin concentration as measured by the thrombin generation. Small symbols represent plasma samples of single donors; large symbols represent controls made of pools of plasma donors.

The generation of thrombin is determined in whole blood or in plasma with different platelet count after activation with phospholipid micelles, which contain tissue factor (1 to 1000 pM tissue factor). Either the maximum thrombin generation (peak thrombin) or the maximum slope of thrombin generation (slope) can be used and based on a calibration curve which is generated by plasmas with—known anti-coagulation (INR values) or a direct procedure for the determination of the INR the INR value of the sample is determined. FIG. 2 shows the correlation between peak thrombin and INR values in different plasmas and calibrators (AK-Calibrant). determined by means of Thrombotest using plasma and phospholipid/tissue factor 71.6 pM.

Example 2

Determination of Thrombophilia

Figure 3:
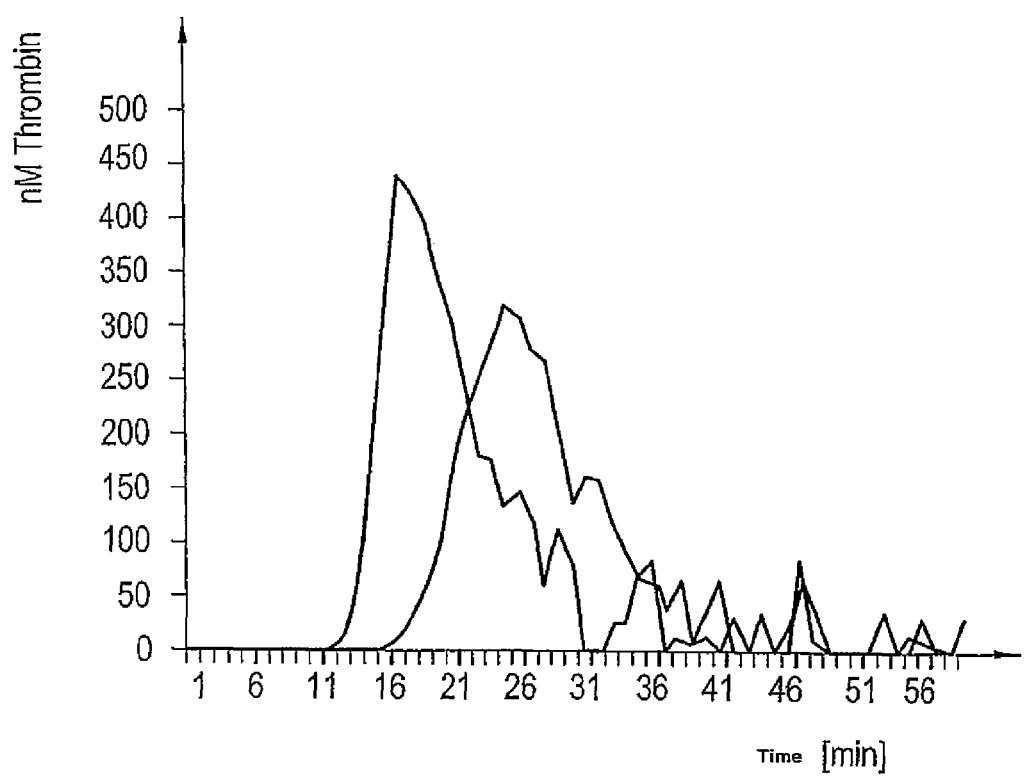
FIG. 3 is a set of curves in which the amount of generated thrombin (nM) is plotted against time in order to compare the result of a thrombin generation assay in a patient with protein C deficiency to that in a normal healthy subject. Protein C deficiency is associated with an increased risk of venous thrombosis.

The generation of thrombin is determined in whole blood or in plasma with different platelet count after activation with phospholipid micelles, which contain tissue factor (1 to 1000 pM tissue factor). Either the maximal thrombin generation (peak thrombin) or the maximum slope of the thrombin generation (Slope) can be used and is compared with the values obtained with a normal sample. An increase in the values over the normal values indicates thrombophilia. FIG. 3 depicts results of TGA from a patient with protein C deficiency (red) compared to a normal patient (blue). In FIG. 3 an example of the values obtained with a patient with deficiency of protein C is shown. Here platelet free plasma and phospholipid tissue factor mixture with 71.6 pM tissue factor were used.

Example 3

Determination of Circulating Micro Particles

Micro particles, derived from platelets, endothelial cells, monocytes and smooth muscle cells, carry on their surface both negatively charged phospholipids as well as tissue factor. Thrombin generation is initiated by micro particles and the amount of formed thrombin is dose-dependent on the amount of micro particles added. This procedure of evaluation of thrombin generation is therefore suitable for the quantitative determination of circulating micro particles.

Thrombin generation is determined on the one hand in platelet rich and platelet poor plasma on the other hand in platelet free plasma using phospholipid micelles which contain no tissue factor to activate coagulation. The difference in the lag phase (time to the beginning of the first thrombin generation after addition of the phospholipid micelles) or the slope or peak thrombin between platelet free (micro-particle-free) plasma and such plasmas which contain platelets or micro-particles is a measure for the content of micro particles in the sample. If isolated micro particles are added to a platelet free (micro-particle free) plasma, a dose-dependent thrombin generation can be determined. As depicted in FIGS. 4 to 7 addition of isolated micro-particles lead to dose-dependent thrombin generation, which can be inhibited by anti-bodies against tissue factor only in case of micro particles derived from monocytes and which is completely dependent on coagulating factor VII likewise only in case of monocytic micro particles. In contrast, thrombin generation by micro particles from endothelial cells does not depend on tissue factor and thus also not on factor VII, however is dependent on factor IX and VIII. Therefore the use of respective deficient plasmas also allows to conclude on the origin of the micro particles.

Figure 4:
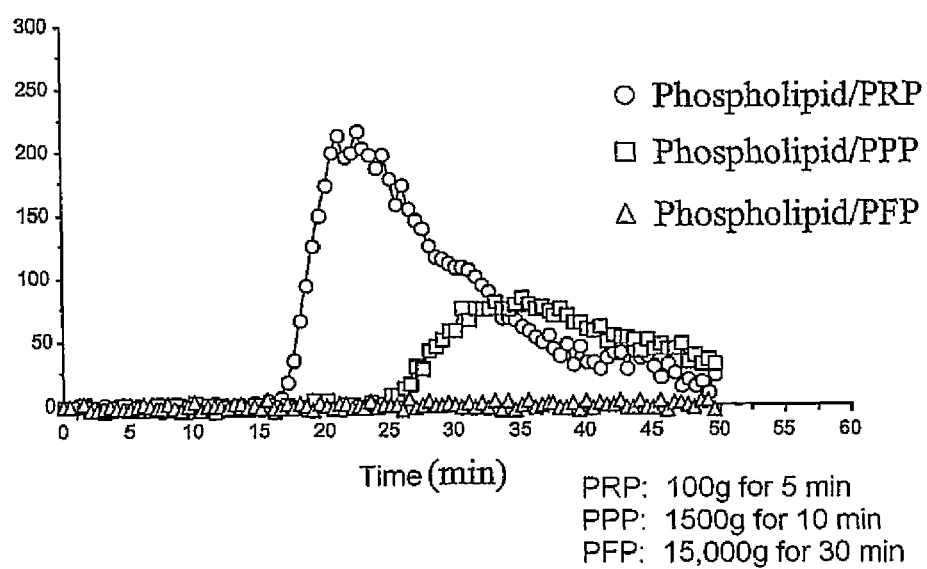
FIG. 4 is a series of graphs showing a thrombin generating assay using phospholipid micelles without tissue factor in platelet-rich, platelet-poor and platelet-free plasma. The amount and velocity of thrombin generated decreases with decreasing the platelet content of the sample.
Figure 5:
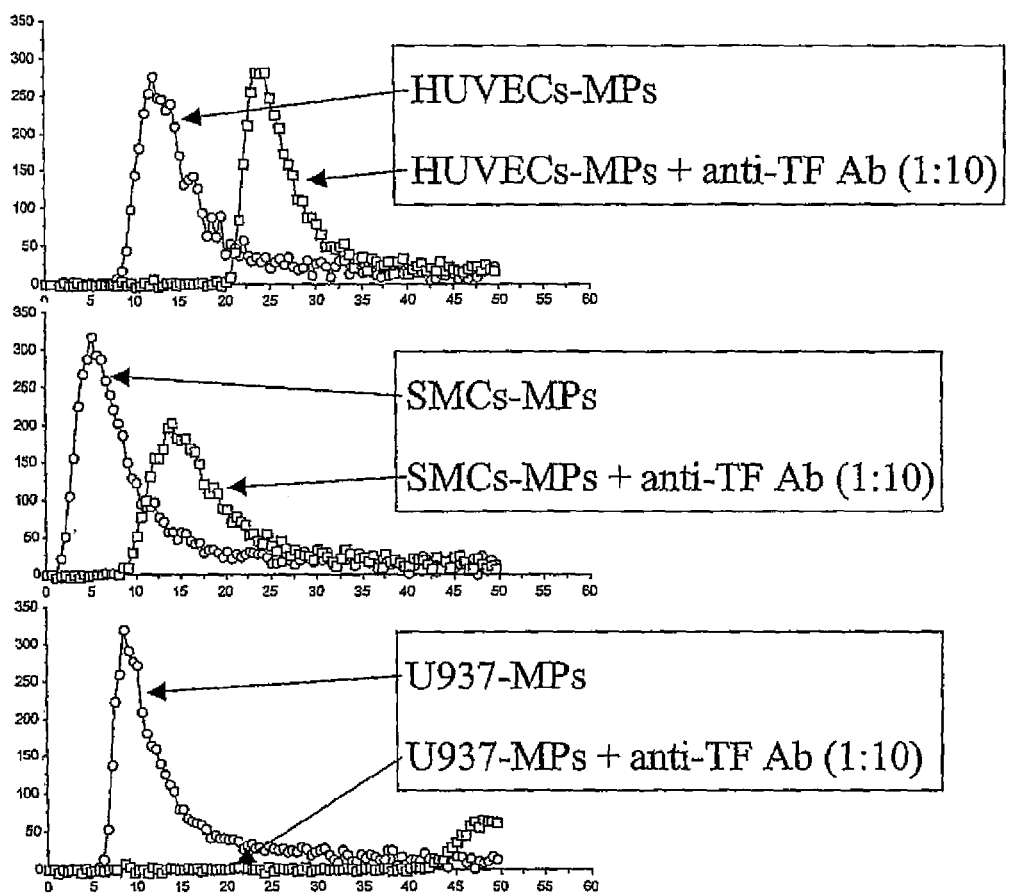
FIG. 5 shows the increasing amount of thrombin generated by increasing numbers of microparticles added to the platelet-free plasma.
Figure 6:
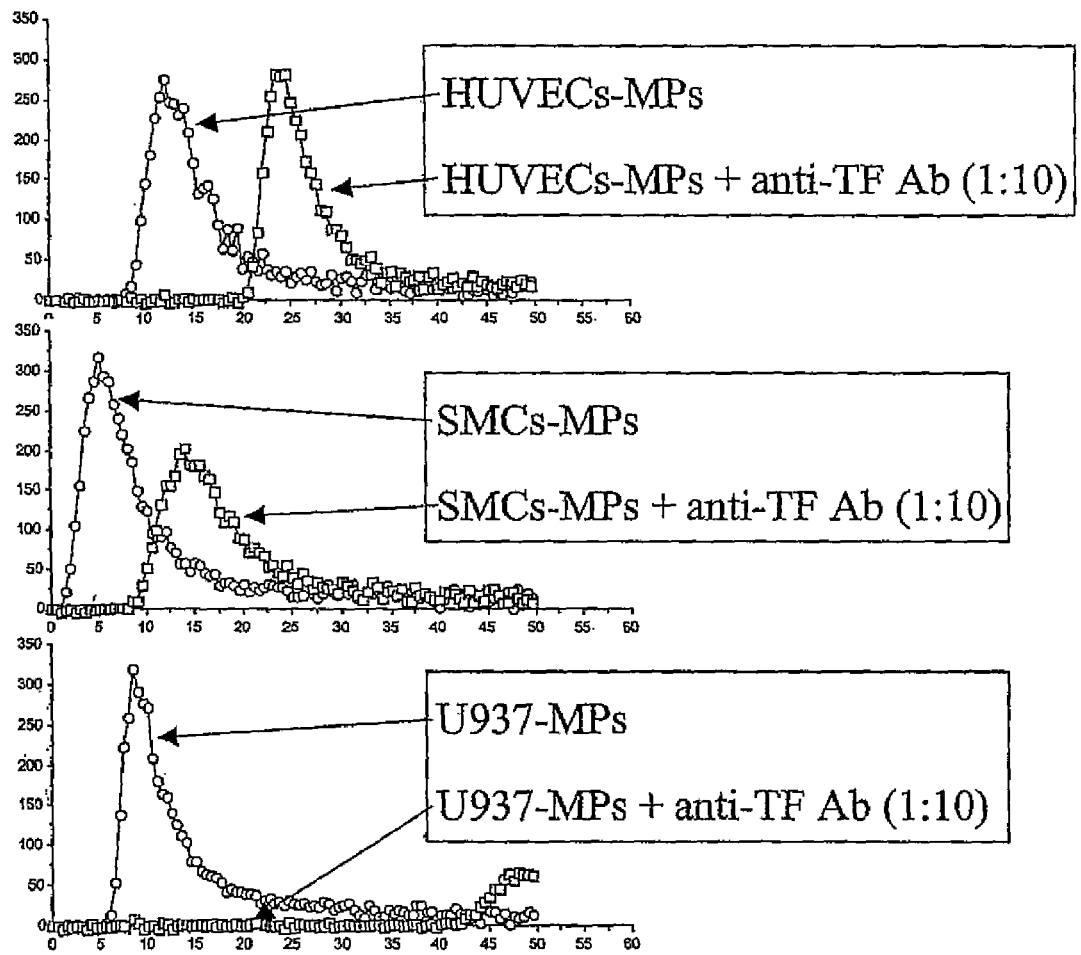
FIG. 6 is a series of graphs showing different levels of thrombin generation by microparticles derived from different cell types. An anti-tissue factor antibody only inhibits thrombin generation in the monocytic derived U937 cell line.
Figure 7:
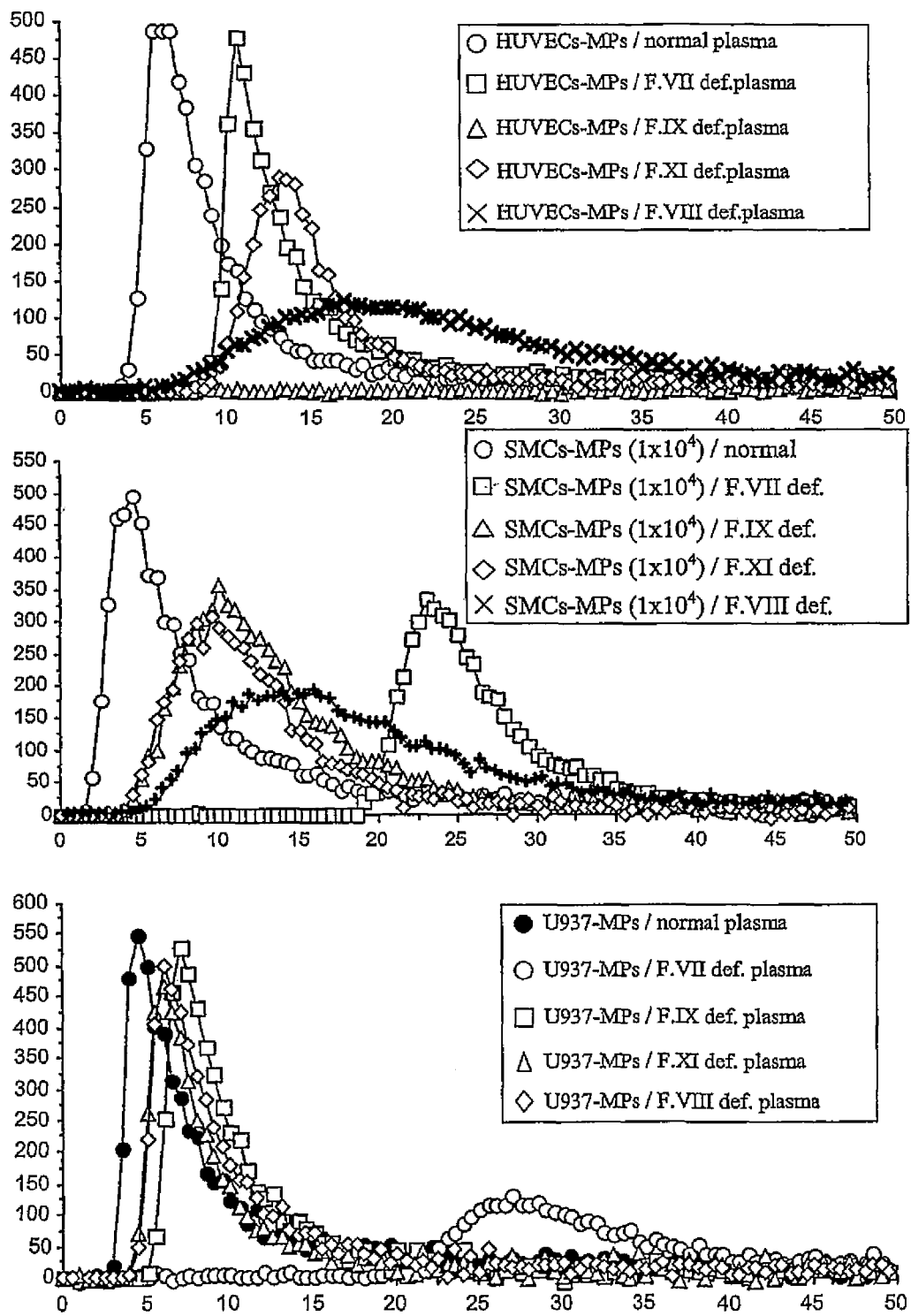
FIG. 7 is a series of graphs showing that thrombin generation by different types of microparticles is dependent upon various coagulation factors. Microparticles were diluted into various factor deficient plasmas as indicated. Only microparticles from monocytes are completely dependent upon FVII. Microparticles from endothelial cells, however, are FVII independent, but dependent upon Factor IX.

FIG. 4 shows thrombin generation by phospholipid micelles without tissue factor in platelet rich (PRP), platelet poor (PPP) and platelet free (PFP) plasma. FIG. 5 shows the dose-dependent thrombin generation by different micro particles. On the abscissa the time is given on the ordinate thrombin generated in nM thrombin per minute. FIG. 6 shows that thrombin generation by different micro particles is differently dependent on tissue factor. An anti-body against tissue factor can only inhibit completely thrombin generation activated by monozytic microparticle. As depicted in FIG. 7 thrombin generation by different micro particles is dependent on various coagulation factors. Only micro particles from monocytes are completely dependent on-factor VII; however, micro-particles from endothelial cells are factor VII independent, but dependent on factor IX.

Example 4

Determination of Thrombin Generation

Usually thrombin generation is determined by means of e.g. fluorigenic substrates in a fluorimeter. Thereby it is however not possible to perform at the same time in the same equipment also regular coagulating test in the respective plasma samples. For the determination of thrombin generation described here an equipment is used, which integrates in the same equipment the possibility to perform normal coagulating tests by means of conventional turbidity measurement, but likewise also the determination of thrombin generation by means of fluorescence measurements. Likewise also the generation of activated factor X can be measured in a similar way. This equipment is characterized by a cuvette ring, which permits the measurement of classical coagulation parameters serially with the parallel measurement of fluorescence. Classical coagulating automats with a measure time of maximally 5 minutes per sample are not suitable the 60 minutes necessary for fluorescence measurement. Only by a cuvette ring such a measurement is made possible.

Example 5

Figure 8:
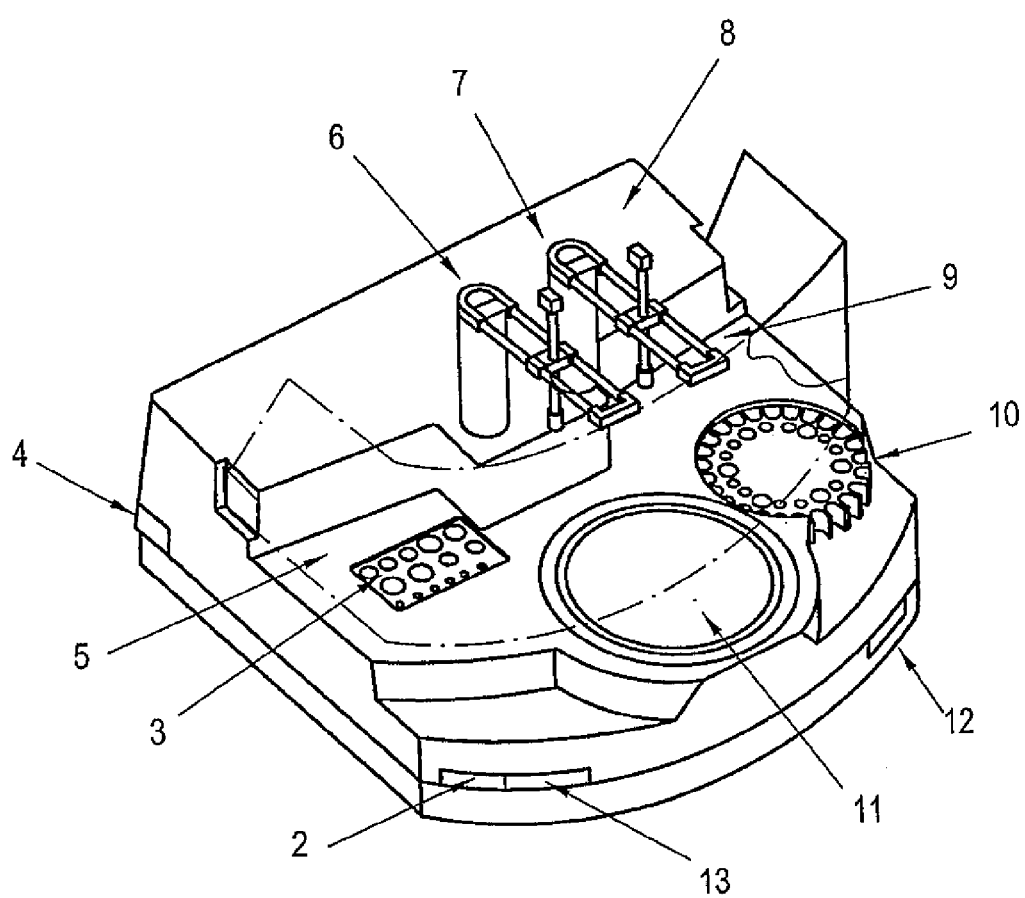
FIG. 8 is a top view drawing, in perspective, of an apparatus designed for parallel determination of thrombin generation by fluorescence measurement and of classical conventional coagulation parameters by turbidity measurement. In the thrombin generation reaction flurophor is emitted by a fluorigenic substrate which is cleaved by thrombin or FXa. These proteases are generated in a blood or plasma sample according to the presented assay of thrombin generation by circulating microparticles.

Equipment for the Parallel Determination of Thrombin Generation by Means of Fluorescence Measurement and of Classical Conventional Coagulation Parameters So far as above mentioned fluorescence measurements and measurements of classical coagulation parameters could only be performed in separate devices. A reason for this is the necessity for fluorescence excitation and measurement of fluorigenic substrates under an angle of optimally 90 degrees and the different measurement time points, which for classical parameters are only some minutes, for which thrombin generation amount however to one hour. By use of a cuvette ring, which can be inserted into a rotating cuvette plate, it is possible that one and the same cuvette is placed at the fluorescence detection position at different time intervals (e.g. minute intervals) and there the fluorescent measurement can be performed, while in another cuvette the incubation for normal coagulating test takes place, which can then be placed on an accordingly neighboring measuring position for turbidity. With not circularly arranged cuvette measuring placed multiple measurements in one cuvette is not possible, without blocking other cuvettes with respect to the conventional measurements. Probes and reagent pipetting is performed conventionally by two sample arms from a sample plate with the respective plasma or blood samples and from the reagent blocks with the appropriate reagents. In FIG. 8 such equipment with a measuring station (1) for two fluorescence measuring positions and for four conventional measuring positions for coagulating, chromogenic substrates and turbidimetric measurements is depicted. The measuring station one contains a bar code scanner (2) and a <12° C. cooled reagent block (3),—four times DIN 22 (2 stirred), 5 times DIN 18 (2 stirred), 5 times Eppendorf tubes. With (4) the main switch is given. The measurement station (1) further contains a reagent block (5) (room temperature, 4 times 25 ml o. DIN 22 bottles), as well as a reagent pipetting arm (6) a sample pipetting arm (7) a dosing pump (8). With (9) the dilution solutions are given (room temperature, 4 times 25 ml o. DIN 22 bottles). The measurement station one shows also a sample plate (10) (24 room temperature), containing 6 controls and calibrators and 12 different reagents as well as a cuvette plate (11) with 6 times 12 cuvettes kept on 37° C. The measuring station (1) is further equipped with a switch (12) and a ROM key (13).

Example 6

Figure 9:
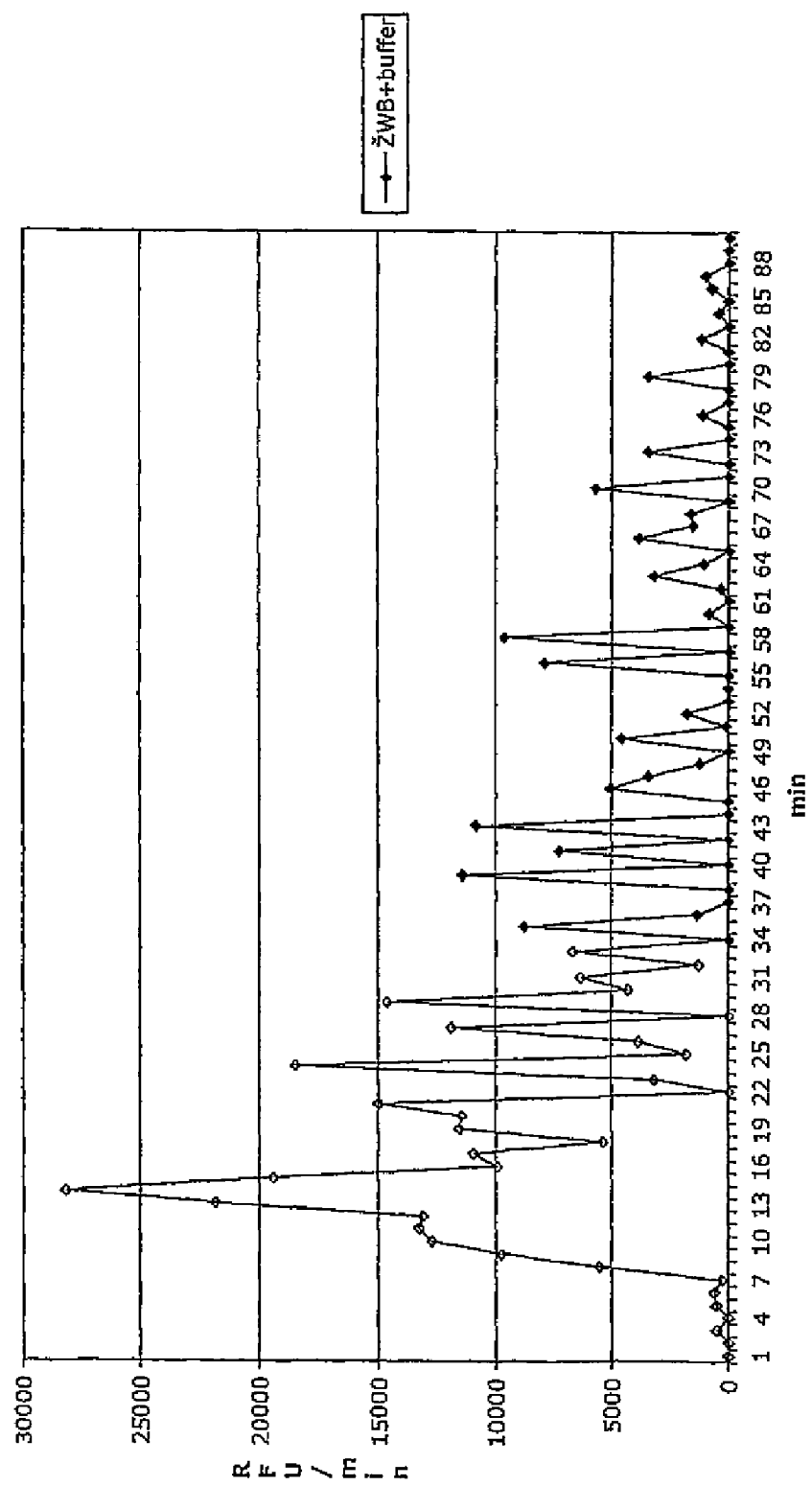
FIG. 9 is a graph showing over time thrombin generation in a sample of whole blood without the benefit of adding a protease inhibitor to prevent the activation of proteases which cleave a fluorigenic substrate and thus interfere with the fluorigenic assay of a sample of whole blood used to determine a patient's ability to generate thrombin, yielding a result that cannot be interpreted.
Figure 10:
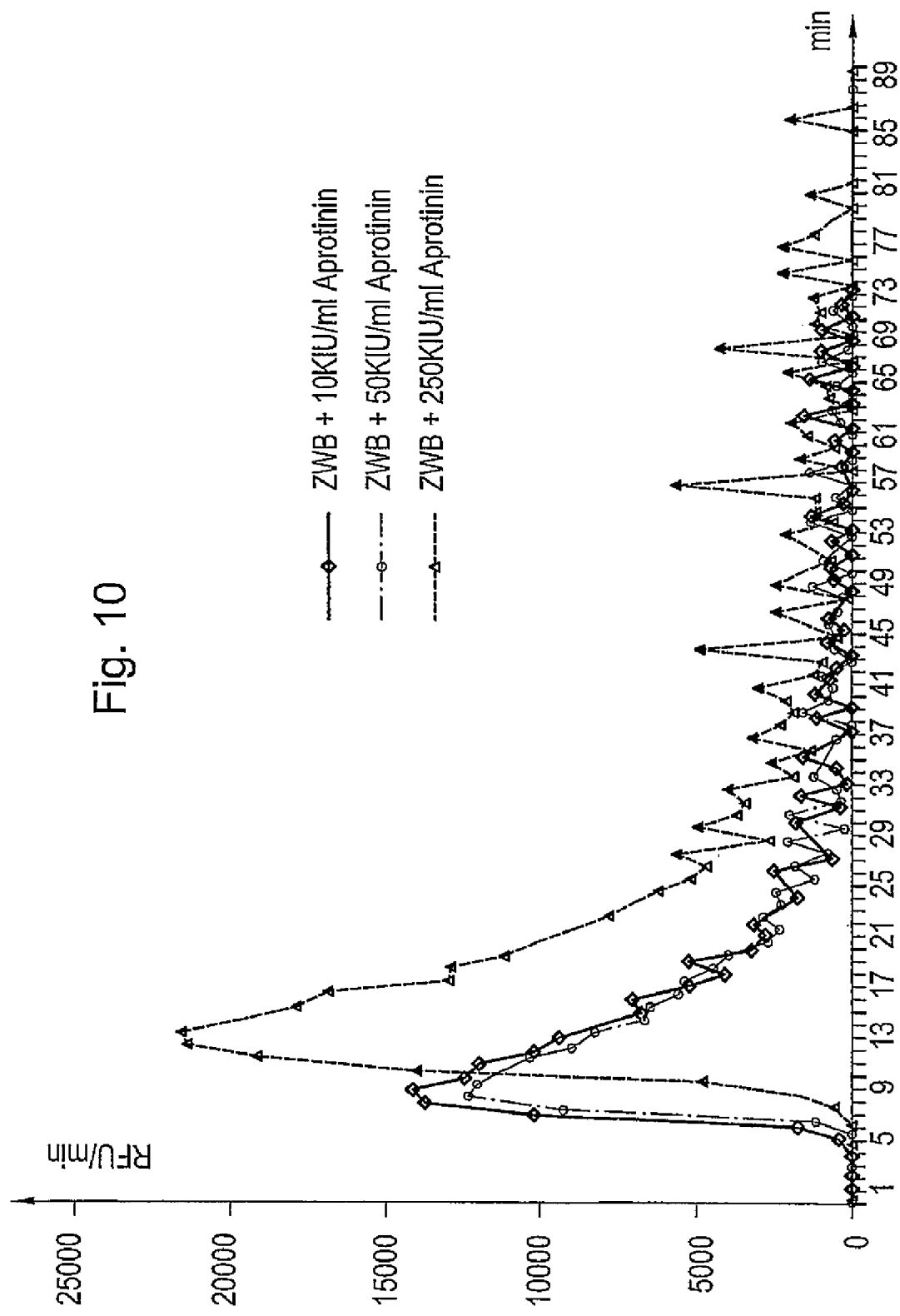
FIG. 10 is a series of graphs showing over time thrombin generation in a sample of whole blood with the benefit of adding Aprotinin as a protease inhibitor, at three different concentrations, to prevent the activation of proteases which cleave a fluorigenic substrate and thus prevent interference with the fluorigenic assay of a sample of whole blood used to determine a patient's ability to generate thrombin, yielding a result that can be interpreted.
Figure 11:
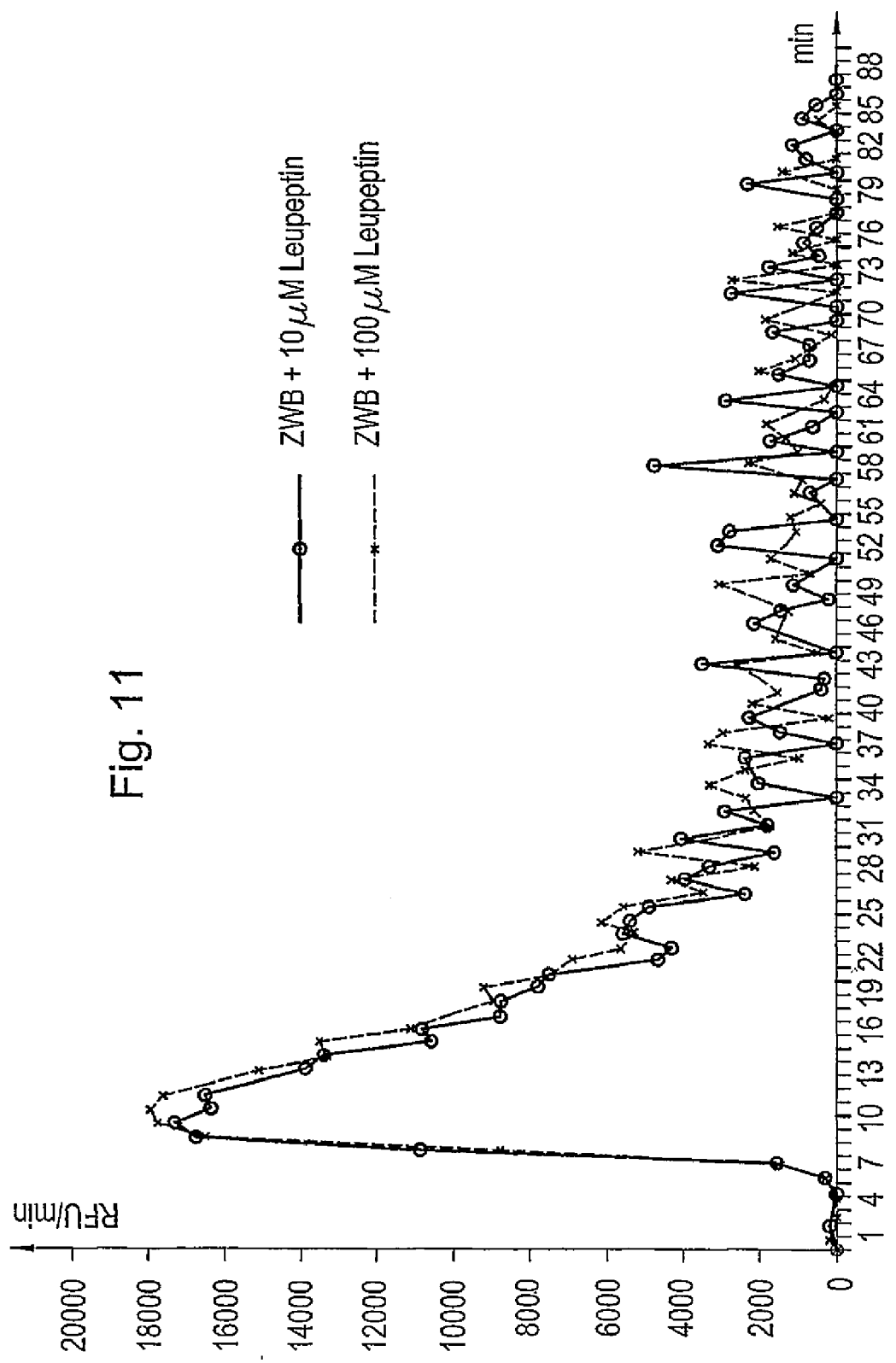
FIG. 11 is a series of graphs showing over time thrombin generation in a sample of whole blood with the benefit of adding Leupeptin as a protease inhibitor, at two different concentrations, to prevent the activation of proteases which cleave a fluorigenic substrate and thus prevent interference with the fluorigenic assay of a sample of whole blood used to determine a patient's ability to generate thrombin, yielding a result that can be interpreted.
Figure 12A:
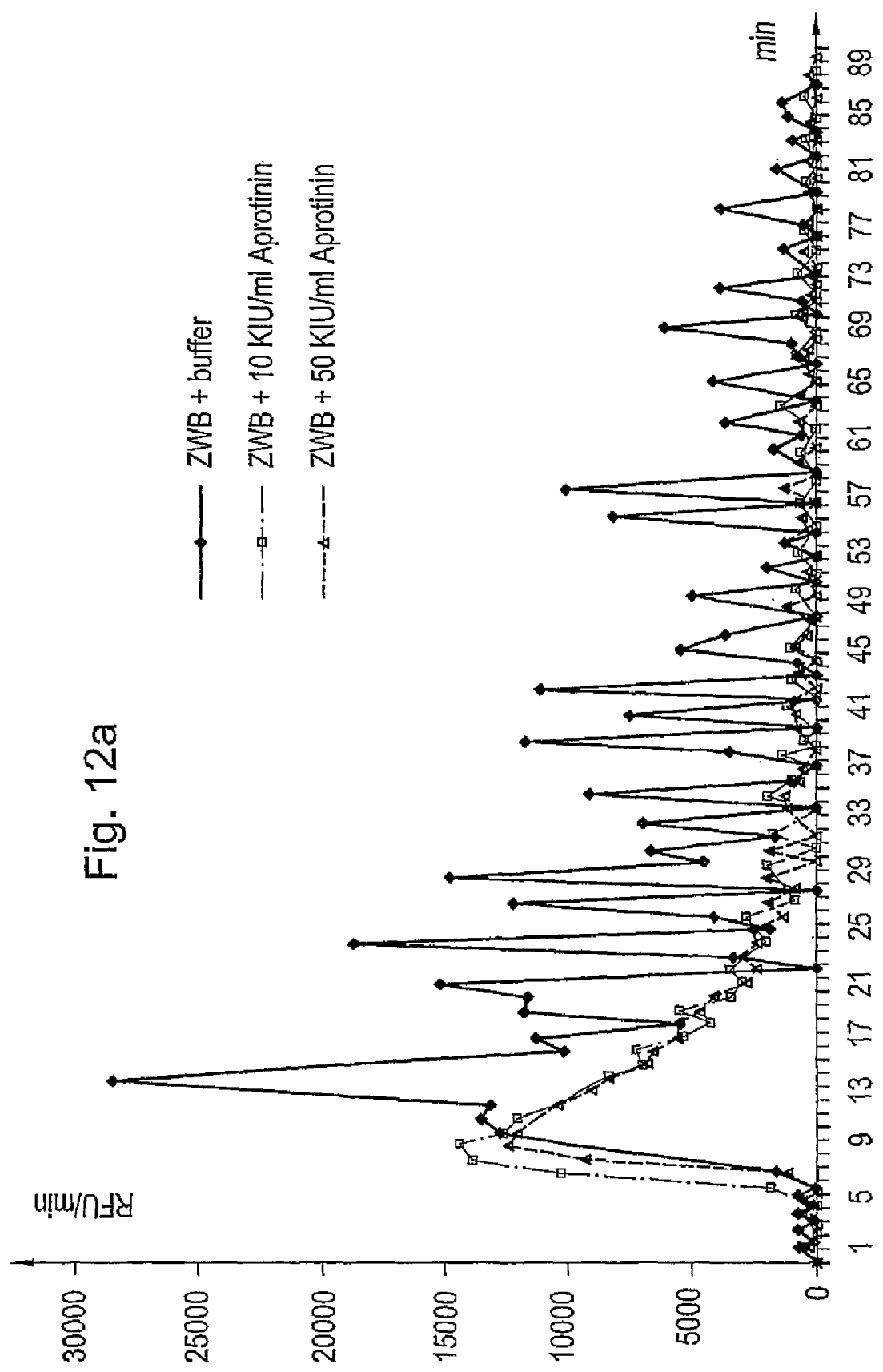
Figure 12C:
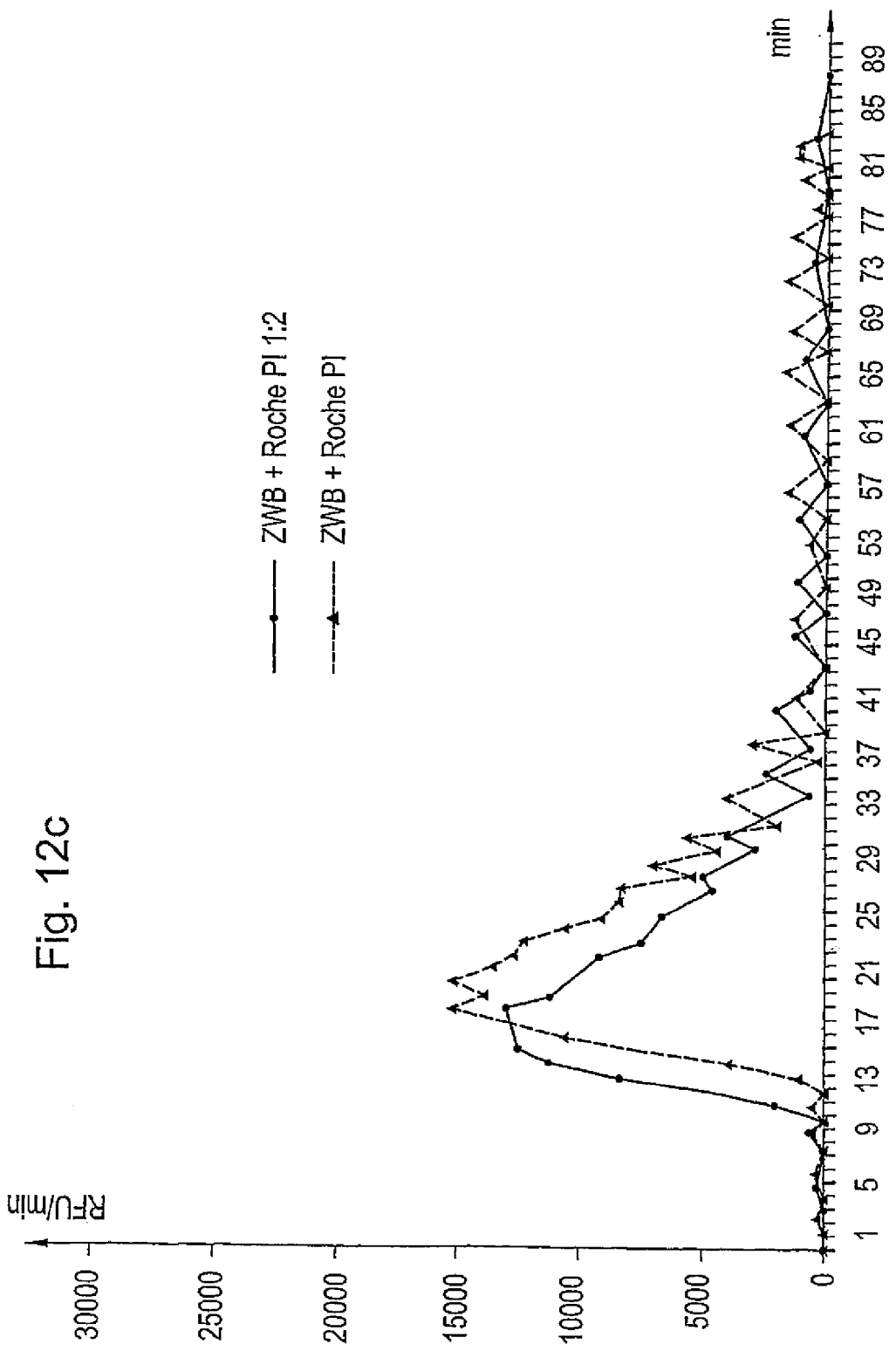

Determination of Thrombin Generation by Means of Fluorescence Measurement in Whole Blood Samples When anticoagulated whole blood is used as sample material for the determination of the thrombin generation, then the danger exists the fact that the results are spoiled by activation of proteolyitic enzymes which cleave the fluoriginic substrate in the same manner as thrombin but are not related to the actual thrombin generation. Thereby it will not be possibly to make an respective quantification of the results. FIG. 9 depicts thrombin generation in whole blood without addition of suitable inhibitors, whereby the results are not easily to be interpreted. To prevent the activation of such different enzymes in particular of leukocyte origin appropriate protease inhibitors in suitable concentrations must be added to the blood sample for the determination of thrombin generation. Such protease inhibitors can include Aprotinin in concentrations between <10 KIU/ml and >250 KIU/ml (FIG. 10 shows the thrombin generation measured in whole blood with the addition of 3 concentrations of Aprotinin, in which the results are interpretable), or with Leupeptin in concentrations of <10 mM and >100 mM (FIG. 11 shows the thrombin generation measured in whole blood with the addition of Leupeptin in 2 concentrations, where the results are interpretable) or a mixture different suitable protease inhibitors (FIG. 12a, FIG. 12b and FIG. 12c shows the determination of thrombin generation measured in whole blood with the addition of different inhibitors or mixtures thereof in different concentrations, where the results are interpretable only in the presence of inhibitors). Only by additive of such inhibitors thrombin generation can be determined in an interpretable way as thrombin generation determined in plasma.

Revealing and the contents of the following literature are part of this patent application

LITERATURE

1. Chantarangkul V, Clerici M, Bressi C et al Thrombin generation assessed as endogenous thrombin potential in patients with hyper- or hypo-coagulability. *Haematologica*. 2003; 88:547-554.
2. Hemker H C, Al Dieri R, Beguin S. Thrombin generation assays: accruing clinical relevance. *Curr Opin Hematol*. 2004; 11:170-175.
3. Lawson J H, Kalafatis M, Stram S et al A model for the tissue factor pathway to thrombin. I. An empirical study. *J Biol Chem*. 1994; 269:23357-23366.

4. Sere K M, Rosing J, Hackeng T M. Inhibition of thrombin generation by protein S at low procoagulant stimuli: implications for maintenance of the haemostatic balance. *Blood.* 2004.
5. Turecek P L, Varadi K, Keil B et al Factor VIII inhibitor-bypassing agents act by inducing thrombin generation and can be monitored by a thrombin generation assay. *Pathophysiol Haemost Thromb.* 2003; 33:16-22.
6. Varadi K, Negrier C, Berntorp E et al Monitoring the bioavailability of FEIBA with a thrombin generation assay. *J Thromb Haemost.* 2003; 1:2374-2380.
7. Varadi K, Siekmann J, Turecek P L et al Phospholipid-bound tissue factor modulates both thrombin generation and APC-mediated factor Va inactivation. *Thromb Haemost.* 1999; 82:1673-1679.
8. Varadi K, Turecek P L, Schwarz H P. Thrombin generation assay and other universal tests for monitoring haemophilia therapy. *Haemophilia.* 2004; 10 Suppl 2:17-21.
9. Ando M, Iwata A, Ozeki Y et al Circulating platelet-derived microparticles with procoagulant activity may be a potential cause of thrombosis in uremic patients. *Kidney Int.* 2002; 62:1757-1763.
10. Bretelle F, Sabatier F, Desprez D et al Circulating microparticles: a marker of procoagulant state in normal pregnancy and pregnancy complicated by preeclampsia or intrauterine growth restriction. *Thromb Haemost.* 2003; 89:486-492.
11. Gonzalez-Quintero V H, Jimenez J J, Jy W et al Elevated plasma endothelial microparticles in preeclampsia. *Am J Obstet Gynecol.* 2003; 189:589-593.
12. Gonzalez-Quintero V H, Smarkusky L P, Jimenez J J et al Elevated plasma endothelial microparticles: preeclampsia versus gestational hypertension. *Am J Obstet Gynecol.* 2004; 191:1418-1424.
13. Sabatier F, Darmon P, Hugel B et al Type 1 and type 2 diabetic patients display different patterns of cellular microparticles. *Diabetes.* 2002; 51:2840-2845.
14. Boulanger C M, Scoazec A, Ebrahimian T et al Circulating microparticles from patients with myocardial infarction cause endothelial dysfunction. *Circulation.* 2001; 104: 2649-2652.
15. Mallat Z, Benamer H, Hugel B et al Elevated levels of shed membrane microparticles with procoagulant potential in the peripheral circulating blood of patients with acute coronary syndromes. *Circulation.* 2000; 101:841-843.
16. Mallat Z, Hugel B, Ohan J et al Shed membrane microparticles with procoagulant potential in human atherosclerotic plaques: a role for apoptosis in plaque thrombogenicity. *Circulation.* 1999; 99:348-353.
17. Dachary-Prigent J, Freyssinet J M, Pasquet J M et al Annexin V as a probe of aminophospholipid exposure and platelet membrane vesiculation: a flow cytometry study showing a role for free sulfhydryl groups. *Blood.* 1993; 81:2554-2565.
18. Freyssinet J M. Cellular microparticles: what are they bad or good for? *J Thromb Haemost.* 2003; 1:1655-1662.
19. Freyssinet J M, Toti F, Hugel B et al Apoptosis in vascular disease. *Thromb Haemost.* 1999; 82:727-735.
20. Freyssinet J M, Mann K G, Meyer D. Phospholipid-binding antibodies and thrombosis. Diagnostica Stago International Symposium, Paris, 14 May 1993. *Blood Coagul Fibrinolysis.* 1993; 4:645-648.
21. Freyssinet J M, Dignat-George F. More on: measuring circulating cell-derived microparticles. *J Thromb Haemost.* 2005.
22. Jy W, Horstman L L, Jimenez J J et al Measuring circulating cell-derived microparticles. *J Thromb Haemost.* 2004; 2:1842-1843.

The invention claimed is:

1. A method of assaying a sample of whole blood or blood plasma from a patient to determine the patient's ability to generate thrombin or Factor Xa as blood-clotting factors, wherein the whole blood or blood plasma contains circulating microparticles of platelets, endothelial cells, monocytes or smooth muscle cells, which comprises the steps of:
   (a) contacting the whole blood or blood plasma sample with a complex comprising phospholipid micelles which contain tissue factor in a concentration of 0 to 1000 pm to activate the circulating microparticles in the whole blood or blood plasma sample to produce thrombin or Factor Xa, and in the case where the sample is a whole blood sample, adding to the whole blood sample, a protease inhibitor to prevent protease activation in the sample;
   (b) following step (a) at a given point in time determining the amount of thrombin or Factor Xa generated by the circulating microparticles, present in the whole blood or blood plasma sample;
   (c) following step (b), at a later given point in time, again determining the amount of thrombin or Factor Xa generated by the circulating microparticles, present in the whole blood or blood plasma sample, according to steps (a) and (b); and
   (d) comparing the difference in the amount of thrombin or Factor Xa generated by the circulating microparticles, present in the whole blood or blood plasma sample, determined according to step (b) and according to step (c), and relating that difference against a standard calibration curve for a whole blood or blood plasma sample analyzed over the same points in time according to steps (a), (b) and (c), to determine the level of thrombin or Factor Xa produced by the circulating microparticles in the whole blood or blood plasma sample, and based upon the determined level of thrombin or Factor Xa produced by the circulating microparticles in the whole blood or blood plasma sample, determining directly the quantity of the circulating microparticles in the whole blood or blood plasma sample and based upon the quantity of the circulating microparticles in the whole blood or blood plasma sample determining the ability of the patient to generate thrombin or Factor Xa as blood clotting factors.

2. The method of assaying a sample of whole blood or blood plasma defined in claim 1 wherein the circulating microparticles of platelets, endothelial cells, monocytes or smooth muscle cells, circulate in the blood and carry on their surfaces both negatively charged phospholipids and tissue factor.

3. The method of assaying a sample of whole blood or blood plasma defined in claim 1 wherein the amount of thrombin generated by the circulating microparticles in the sample of whole blood or blood plasma is determined by measuring the change in fluorescence generated by the thrombin between step (b) and step (c).

4. The method of assaying a sample of whole blood or blood plasma defined in claim 1 wherein the phospholipid micelles contain tissue factor and wherein calcium chloride is added to the sample of whole blood or blood plasma before the circulating microparticles begin to generate thrombin.

5. A method of assaying circulating microparticles contained in a sample of whole blood or blood plasma from a patient to determine the patient's ability to generate thrombin or Factor Xa as blood-clotting factors, wherein the circulating microparticles are microparticles of platelets, endothelial cells, monocytes, or smooth muscle cells, which carry on their surfaces both negatively charged phospholipids as well as tissue factor, which comprises the steps of:

(a) contacting the whole blood or blood plasma sample with a complex comprising phospholipid micelles to activate the circulating microparticles in the whole blood or blood plasma sample to produce thrombin or Factor Xa, and in the case where the sample is a whole blood sample, adding to the whole blood sample, a protease inhibitor to prevent protease activation in the sample;

(b) following step (a) at a given point in time determining the amount of thrombin or Factor Xa generated by the circulating microparticles, present in the whole blood or blood plasma sample;

(c) following step (b), at a later given point in time, again determining the amount of thrombin or Factor Xa generated by the circulating microparticles, present in the whole blood or blood plasma sample; and (d) comparing the difference in the amount of thrombin or Factor Xa generated by the circulating microparticles, present in the whole blood or blood plasma sample, determined according to step (b) and according to step (c), and relating that difference against a standard calibration curve for a whole blood or blood plasma sample analyzed over the same points in time according to steps (a), (b), and (c), to determine the level of thrombin or Factor Xa produced by the circulating microparticles in the whole blood or blood plasma sample, and based upon the determined level of thrombin or Factor Xa, determining directly the quantity of the circulating microparticles in the whole blood or blood plasma sample, and based upon the quantity of the circulating microparticles in the whole blood or blood plasma sample, determining the ability of the patient to generate thrombin or Factor Xa as blood clotting factors.

6. A method of assaying circulating microparticles contained in a sample of whole blood or blood plasma from a patient to determine the patient's ability to generate thrombin or Factor Xa as blood-clotting factors, wherein the circulating microparticles are microparticles of platelets, endothelial cells, monocytes, or smooth muscle cells, which carry on their surfaces both negatively charged phospholipids as well as tissue factor, which comprises the steps of:

(a) contacting the whole blood or blood plasma sample with a complex comprising phospholipid micelles which contain tissue factor in a concentration of 1 to 1000 pm, together with calcium chloride, to activate the circulating microparticles in the whole blood or blood plasma sample, to produce thrombin or Factor Xa, and in the case where the sample is a whole blood sample, adding to the whole blood sample, a protease inhibitor to prevent protease activation in the sample;

(b) following step (a) at a given point in time determining the amount of thrombin or Factor Xa generated by the circulating microparticles, present in the whole blood or blood plasma sample;

(c) following step (b), at a later given point in time, again determining the amount of thrombin or Factor Xa generated by the circulating microparticles, present in the whole blood or blood plasma sample; and (d) comparing the difference in the amount of thrombin or Factor Xa generated by the circulating microparticles, present in the whole blood or blood plasma sample, determined according to step (b) and according to step (c), and relating that difference against a standard calibration curve for a whole blood or blood plasma sample analyzed over the same points in time according to steps (a), (b), and (c), to determine the level of thrombin or Factor Xa produced by the circulating microparticles in the whole blood or blood plasma sample, and based upon the determined level of thrombin or Factor Xa, determining directly the quantity of the circulating microparticles in the whole blood or blood plasma sample, and based upon the quantity of the circulating microparticles in the whole blood or blood plasma sample, determining the ability of the patient to generate thrombin or Factor Xa as blood clotting factors.

7. A method of assaying circulating microparticles contained in a sample of anticoagulated whole blood from a patient to determine the patient's ability to generate thrombin as a blood-clotting factor, wherein the whole blood contains circulating microparticles of platelets, endothelial cells, monocytes, or smooth muscle cells, which carry on their surfaces both negatively charged phospholipids as well as tissue factor, which comprises the steps of:

(a) contacting the anticoagulated whole blood sample with a complex comprising phospholipid micelles, to activate the circulating microparticles in the whole blood sample to produce thrombin;

(b) adding to the anticoagulated whole blood sample, a protease inhibitor to prevent protease activation in the sample;

(c) following steps (a) and (b) at a given point in time determining the amount of thrombin generated by the circulating microparticles, present in the anticoagulated whole blood sample, by contacting the anticoagulated whole blood sample with a fluorigenic substrate cleavable by thrombin and detecting an amount of fluorescence generated by cleavage of the fluorigenic substrate by the thrombin in the anticoagulated whole blood sample;

(d) following step (c), at a later given point in time, again determining the amount of thrombin generated by the circulating microparticles, present in the whole blood sample by again contacting the anticoagulated whole blood sample with a fluorigenic substrate cleavable by thrombin and detecting an amount of fluorescence generated by cleavage of the fluorigenic substrate by the thrombin in the anticoagulated whole blood sample; and (e) comparing the difference in the amount of thrombin generated by the circulating microparticles, present in the whole blood sample, determined according to step (c) and according to step (d), and relating that difference against a standard calibration curve for a whole blood sample analyzed over the same points in time according to steps (a), (b), (c), and (d), to determine the level of thrombin produced by the circulating microparticles in the whole blood sample, and based upon the determined level of thrombin, determining directly the quantity of the circulating microparticles in the whole blood sample, and based upon the quantity of the circulating microparticles in the whole blood sample, determining the ability of the patient to generate thrombin as a blood clotting factor.

8. A method of assaying circulating microparticles contained in a sample of anticoagulated whole blood from a patient to determine the patient's ability to generate thrombin as a blood-clotting factor, wherein the whole blood contains circulating microparticles of platelets, endothelial cells, monocytes, or smooth muscle cells, which carry on their surfaces both negatively charged phospholipids as well as tissue factor, which comprises the steps of:

(a) contacting the anticoagulated whole blood sample with a complex comprising phospholipid micelles, which contain tissue factor in a concentration of 1 to 1000 ρm, together with calcium chloride, to activate the circulating microparticles in the whole blood sample to produce thrombin;

(b) adding to the anticoagulated whole blood sample, a protease inhibitor to prevent protease activation in the sample;

(c) following steps (a) and (b) at a given point in time determining the amount of thrombin generated by the circulating microparticles, present in the anticoagulated whole blood sample, by contacting the anticoagulated whole blood sample with a fluorigenic substrate cleavable by thrombin and detecting an amount of fluorescence generated by cleavage of the fluorigenic substrate by the thrombin in the anticoagulated whole blood sample;

(d) following step (c), at a later given point in time, again determining the amount of thrombin generated by the circulating microparticles, present in the whole blood sample by again contacting the anticoagulated whole blood sample with a fluorigenic substrate cleavable by thrombin and detecting an amount of fluorescence generated by cleavage of the fluorigenic substrate by the thrombin in the anticoagulated whole blood sample; and (e) comparing the difference in the amount of thrombin generated by the circulating microparticles, present in the whole blood sample, determined according to step (c) and according to step (d), and relating that difference against a standard calibration curve for a whole blood sample analyzed over the same point in time according to steps (a), (b), (c), and (d), to determine directly the level of thrombin produced by the circulating microparticles in the whole blood sample, and based upon the determined level of thrombin, determining the quantity of the circulating microparticles in the whole blood sample, and based upon the quantity of the circulating microparticles in the whole blood sample, determining the ability of the patient to generate thrombin as a blood clotting factor.

* * * * *